US006841388B2

(12) United States Patent
Dukor et al.

(10) Patent No.: US 6,841,388 B2
(45) Date of Patent: Jan. 11, 2005

(54) METHOD AND SYSTEM FOR DIAGNOSING PATHOLOGY IN BIOLOGICAL SAMPLES BY DETECTION OF INFRARED SPECTRAL MARKERS

(75) Inventors: Rina K. Dukor, Lake Zurich, IL (US); Curtis A. Marcott, Cincinnati, OH (US)

(73) Assignees: Vysis, Inc., Downers Grove, IL (US); Procter & Gamble, Cincinnati, OH (US)

( * ) Notice: Subject to any disclaimer, the term of this patent is extended or adjusted under 35 U.S.C. 154(b) by 186 days.

(21) Appl. No.: 09/996,205

(22) Filed: Nov. 28, 2001

(65) Prior Publication Data

US 2002/0164810 A1 Nov. 7, 2002

Related U.S. Application Data

(60) Provisional application No. 60/254,772, filed on Dec. 5, 2000, and provisional application No. 60/251,447, filed on Dec. 5, 2000.

(51) Int. Cl.[7] .............................................. G01N 21/62
(52) U.S. Cl. ........................ 436/64; 436/164; 436/171; 356/51; 356/300; 356/303; 356/317; 356/451; 250/339.02; 250/339.08; 382/128
(58) Field of Search ........................... 436/63, 64, 164, 436/171; 356/51, 300, 303, 306, 317–320, 451; 250/339.02, 339.08; 382/128

(56) References Cited

U.S. PATENT DOCUMENTS

| | | | |
|---|---|---|---|
| 5,539,207 A | | 7/1996 | Wong |
| 5,596,992 A | | 1/1997 | Haaland et al. |
| 5,945,674 A | * | 8/1999 | Dukor ................... 250/339.11 |
| 6,146,897 A | * | 11/2000 | Cohenford et al. ............ 436/63 |
| 6,274,871 B1 | * | 8/2001 | Dukor et al. .......... 250/339.08 |
| 6,697,665 B1 | * | 2/2004 | Rava et al. .................. 600/475 |
| 2002/0010400 A1 | * | 1/2002 | Camacho et al. ........... 600/473 |

OTHER PUBLICATIONS

Max Deim, Susie Boydston–White, and Luis Chiriboga, Infrared Spectroscopy of Cells and Tissue: Shining Light onto a Novel Subject; Focal Point, The Society for Applied Spectroscopy Departments of Chemistry and Biochemistry, City University of New York, Hunter College; vol. 53, No. 4, Apr. 1999, pp. 148A–161A.

E. Neil Lewis, Patrick J. Treado, Robert C. Reeder, Gloria M. Story, Anthony E. Dowrey, Curtis Marcott, and Ira W. Levin, Fourier Transform Spectroscopic Imaging Using an Infrared Focal–Plane Array Detector; Analytical Chemistry, vol. 67 No. 19, Oct. 1, 1995, p. 3377–3381.

Story G M et al: Infrared Spectroscopic Imaging: A New Tool for the Pathology Laboratory, Breast Cancer Research and Treatment vol. 64, No. 1, Nov. 2000, p. 59.

Dukor Rina K et al., A Method for Analysis of Clinical Tissue Samples Using FTIR Microspectroscopic imaging, Spectroscopy of Biological Molecules, New Direction 1999, pp. 471–472.

* cited by examiner

Primary Examiner—Maureen M. Wallenhorst
(74) Attorney, Agent, or Firm—Leydig, Voit & Mayer, Ltd.

(57) ABSTRACT

A method and system for diagnosing pathology, such as carcinoma, in a biological sample identifies presence of pathology based on the existence of an infrared markers in the extracellular material, rather than cells, in the biological sample. In the case of breast cancer diagnosis, an effective marker is a baseline slope of a 1280 $cm^{-1}$ band in the infrared spectra of connective tissue, with normal biopsy samples exhibiting a positive slope and cancerous samples showing a relatively flat baseline. Infrared spectroscopy, both microscopic and macroscopic, may be used to identify a sample region containing extracellular material and to collect infrared absorbance data, from which the existence of the pathology marker is determined.

15 Claims, 6 Drawing Sheets

METHOD AND SYSTEM FOR DIAGNOSING PATHOLOGY IN BIOLOGICAL SAMPLES BY DETECTION OF INFRARED SPECTRAL MARKERS

FIELD OF THE INVENTION

This invention relates generally to the examination of biological samples for diagnosis of pathology, such as carcinoma. More particularly, the invention relates to the use of infrared spectroscopy to examine biological samples for identifying spectral features indicative of the presence of pathology.

BACKGROUND OF THE INVENTION

In disease treatment and prevention, early and reliable detection of pathology or the risk for developing pathology is invaluable. For instance, breast cancer is the second leading cause of cancer related death in women. Data indicate that ninety-six percent of women will survive five years if the cancer is localized, seventy-five percent will survive five years if the cancer is regional, and twenty percent will survive for that period of time if the cancer is metastasized. A method that can effectively and reliably identify breast cancer can lead to prompt treatments and improve the chances of survival for breast cancer patients.

Conventionally, pathology diagnosis typically involves the study of a biological sample, such as a biopsy of breast tissue, by a trained pathologist. In the past decade or so, however, applications of spectroscopy and microspectroscopy have made great advancements in the areas of clinical study. Several laboratories are currently actively investigating the potential of various spectroscopic techniques for screening and pathology diagnosis.

For instance, infrared microspectroscopy has been used in the study of cellular material. As is well known, infrared microspectroscopy involves illuminating a sample being studied with infrared light, and collecting the infrared light from a selected microscopic region of the sample to derive the infrared absorption spectrum of that region. Recently, Fourier Transform Infrared (FT-IR) spectroscopic imaging microscopy has been developed into a very powerful analytical technique. This technique uses a focal-plane array (FPA) detector attached to an FT-IR microscope to collect infrared images of an area of interest on the sample at various wavenumbers. The FPA detector includes an array (for example, 64×64 or 256×256) of pixels, each capable of independently detecting the intensity of infrared light impinging thereupon. A significant advantage of this technique as compared to more conventional infrared microspectroscopy is the parallel infrared detection using a relatively large number of pixels, which eliminates the need of point-by-point mapping of the sample. The parallel detection significantly reduces the time required to collect infrared images and spectra of a given sample.

Additional examples and direction of infrared microspectroscopic imaging are provided, for example, by Marcott et al., "Infrared Microspectroscopic Imaging of Biomineralized Tissues Using a Mercury-Cadmium-Telluride Focal-Plane Array Detector," *Cellular and Molecular Biology* 44(1), 109–115 (February 1998); Lewis et al., "Fourier Transform Spectroscopic Imaging Using an Infrared Focal-Plane Array Detector," *Analytical Chemistry* 67(19), 3377–3381 (Oct. 1, 1995); and U.S. Pat. No. 5,377,003 to Lewis. These references are hereby incorporated herein by reference.

Teachings in the prior art regarding the use of infrared spectroscopy for evaluation of cervical cells for malignancy or pre-malignant conditions are found, for example, in U.S. Pat. Nos. 5,976,885 and 6,031,232, both to Cohenford. The prior art also teaches a method for machine-based collection and interpretation of data on cells and tissues using vibrational spectroscopy. See, for example, U.S. Pat. No. 5,733,739 to Zakim, and U.S. Pat. No. 5,596,992.

Conventionally, infrared spectroscopic studies of biological samples have focused on cellular materials in the samples, with attempts to identify spectral features of the cells that could be linked to the presence of pathology. To date, many such attempts have been made. Yet, to the knowledge of the inventors of the present invention, no spectral features from extracellular materials in biological samples have been reliably correlated to common pathological conditions such as carcinoma.

SUMMARY OF THE INVENTION

In view of the foregoing, the present invention provides a method and system for diagnosing pathology in a biological sample using infrared spectroscopy. In accordance with a feature of the invention, an infrared spectrum is taken from a region of the biological sample that contains an extracellular material, such as connecting tissue, rather than from cells in the sample. The infrared spectrum of the extracellular material is analyzed to identify the existence of a spectral feature or marker that is found in samples with the presence of the pathology but not in normal (or healthy) samples. As used herein, the term "marker" may be the spectral feature itself or a quantity or condition derived from spectral data that is indicative of the existence of the spectral feature. Finding the infrared spectral marker in the biological sample being studied indicates the presence of pathology in that sample.

In particular, the invention shows that the existence of a peak or shoulder in the infrared spectrum of a biological sample around the wavenumber of 1280 cm$^{-1}$ is effective for pathology detection, especially carcinoma. A marker used to indicate the existence of this spectral feature is the baseline slope of the 1280 cm$^{-1}$ band. For breast biopsy samples from patients diagnosed by pathologists as having breast cancer, the 1280 cm$^{-1}$ band is riding on a relatively flat baseline. In contrast, in spectra taken from samples from cancer-free patients, the baseline associated with the 1280 cm$^{-1}$ band has a significantly positive slope.

To identify the existence of such a marker, infrared absorption spectral data are preferably collected using an infrared imaging device having a focal-plane array (FPA) detector. In accordance with a feature of an embodiment, to facilitate efficient data acquisition and analysis of the baseline slope of the 1280 cm$^{-1}$ band, two filters with narrow pass bands around two wavenumbers on the two sides of the marker band, such as about 1303 cm$^{-1}$ and 1264 cm$^{-1}$, may be used with an infrared source to enable efficient determination of the infrared absorption spectral intensities at the two wavenumbers. The intensities at the two wavenumbers are then used to determine the baseline slope of the 1280 cm$^{-1}$ band. The calculations of this baseline slope may be performed automatically on measured infrared data by a computer programmed for such infrared spectral analysis.

The intensity data for deriving the 1280 cm$^{-1}$ marker may be scaled to the amount of extracellular tissue present in the measured sample region, which is indicated by the measured intensity (peak height or peak area) of an infrared absorption peak around 1340 cm$^{-1}$. To that end, in accordance with a feature of an embodiment, an infrared imaging device is equipped with four filters with narrow pass bands centered about 1264 cm⁻¹, 1303 cm⁻¹, 1340 cm⁻¹, and 1366 cm⁻to measure the intensities of the infrared spectrum at these wavenumbers, from which the baseline slope of the 1280 cm⁻¹ band and the corrected 1340 cm⁻¹ peak intensity (are derived and used in the scaling calculation.

In accordance with a feature of an embodiment, a macroscopic infrared reflectance imaging device is used for taking infrared images of a biological sample mounted on an infrared-reflective surface. The imaging device includes an infrared source, at least a filter of a narrow bandwidth at a desired wavenumber, a first lens and a first mirror for directing the output of the infrared source through the filter toward the biological sample for illumination thereof, and a second lens and a second mirror for focusing infrared light from the sample onto a detector array. In other embodiments, focusing mirrors may be used in place of the two lenses.

In addition to reflectance, these experiments could be preformed in transmittance mode, either microscopically or macroscopically, with either an FPA, linear array, or single-element IR detector.

Other objects and advantages will become apparent with reference to the following detailed description when taken in conjunction with the drawings.

Figure 1:
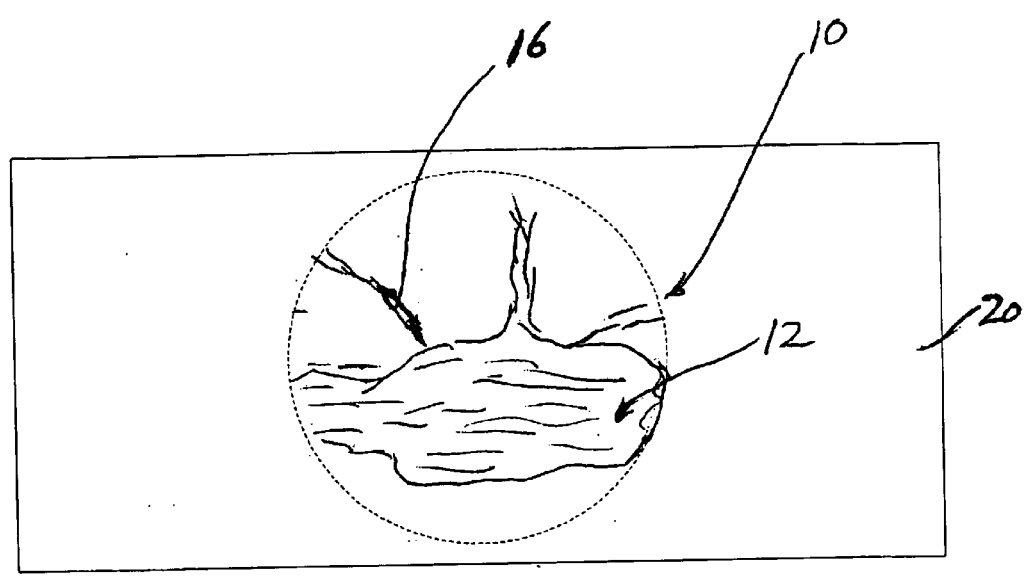
FIG. 1 is a schematic presentation of a biological sample containing extracellular materials.

While the invention is susceptible to various modifications and alternative constructions, certain illustrated embodiments have been shown in the drawings and will be described below. It should be understood, however, that there is no intention to limit the invention to the specific forms disclosed, but, on the contrary, the invention is to cover all modifications, alternative constructions and equivalents falling within the spirit and scope of the invention as defined by the appended claims.

DETAILED DESCRIPTION OF THE PREFERRED EMBODIMENT

The present invention is based on the discovery that the infrared spectra of the extracellular material in a biological sample may carry a spectral feature, or "marker," that is a signature of presence of pathology in the sample.

Conventionally, when infrared spectroscopy is applied to analyses of biological samples, the focus is on the cells in the sample. In other words, infrared spectra of the cells are studied with the hope that they contain information that can be used to identify whether the sample contains pathology, such as carcinoma.

In sharp contrast to the conventional approach, the present invention has shown that the extracellular material in a biological sample, rather than the cells, may exhibit a marker in its infrared absorption spectrum that is indicative of the presence of pathology. By way of example, FIG. 1 shows, in a schematic manner, a magnified view of a biological sample 10 that is in the form of a thin layer supported on a substrate 20 suitable for infrared spectroscopic studies, as will be described in greater detail below. The biological sample includes a region 12 that contains cells, and another region 16 that contains extracellular material (i.e., material outside the cells). One particular example of such a biological sample is a breast biopsy sample for breast cancer diagnosis. The extracellular material in that example may be, for instance, connective tissue.

To practice the invention, the region 16 in the biological sample 10 is identified as containing extracellular material. Infrared absorption spectral measurements are performed on that region either in the reflective mode or in the transmission mode. The measured infrared absorbance data are used to determine whether the sample region containing extracellular material exhibits an infrared spectral marker indicative of a pathological condition. The correlation between the marker and the pathology has been pre-established by comparing infrared spectra of samples having pathology with infrared spectra of normal samples (i.e., samples without the presence of the pathology). The existence of the marker in the extracellular material of the biological sample being studied is then an indication that the sample contains pathology.

Figure 2:
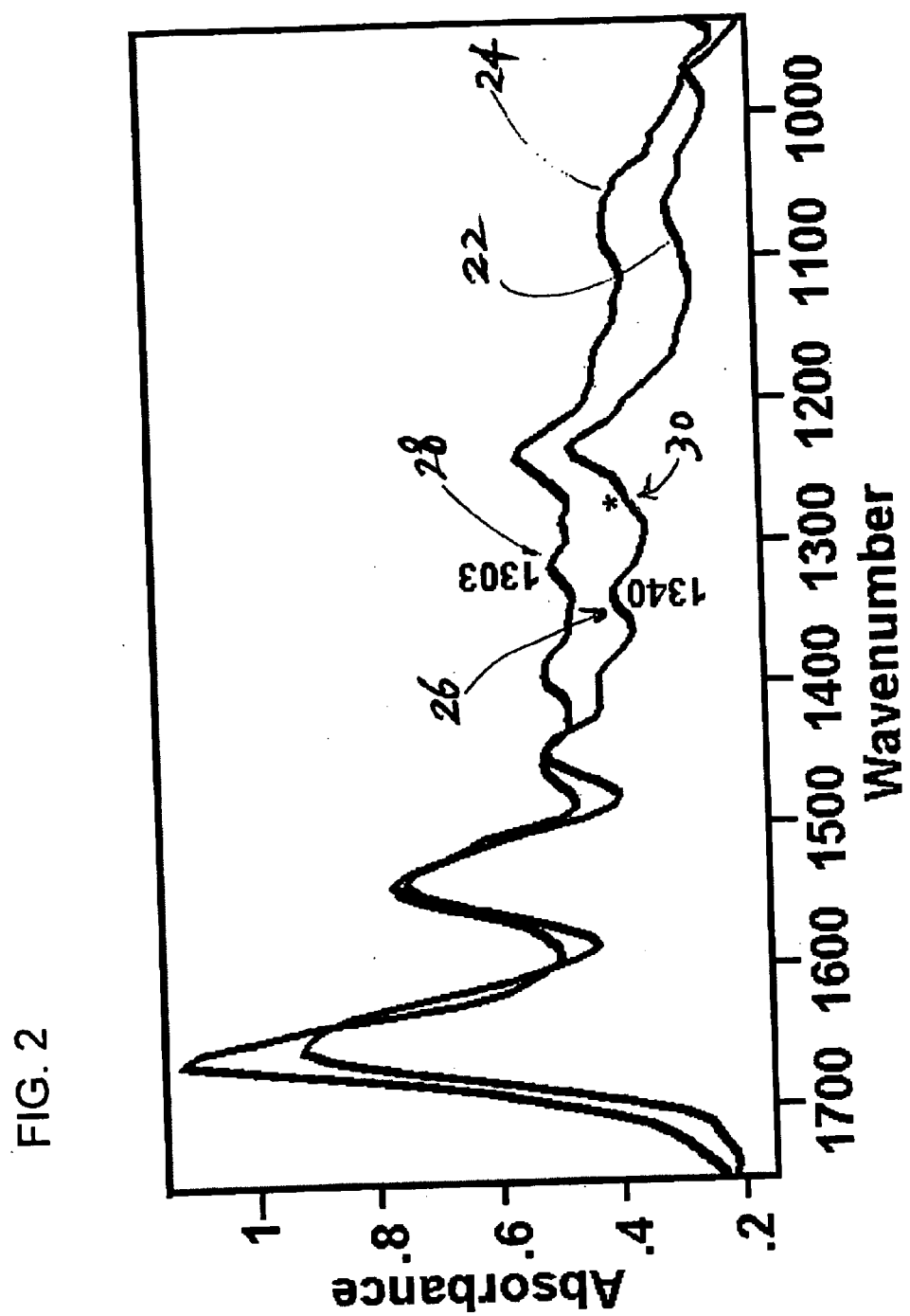
FIG. 2 shows mid-infrared absorbance spectra taken from two regions of a biological sample containing cells and extracellular material, respectively.

One very important example of the application of the invention is the clinical diagnosis of breast cancer by means of infrared spectroscopic studies of breast biopsy samples. FIG. 2 shows two mid-infrared spectra taken from a breast biopsy sample. As will be described in greater detail below, the sample was mounted on a substrate that transmits visual light but reflects infrared light to allow the same sample to be studied by both conventional pathological inspection and infrared absorbance spectroscopy in the reflective mode. One spectrum 22 in FIG. 2 is taken from a region of the sample visually identified (i.e., by means of conventional pathological study) as containing mainly connective tissue. The other spectrum 24 is taken from a region of the same sample that contains mainly epithelial cells. It can be seen that there are clear differences in the infra spectra of the cells and the connective tissue (extracellular material). In particular, the spectrum 22 has a band 26 at 1340 cm⁻¹, which always appears in connective tissue. As will be described in greater detail below, the 1340 cm⁻¹ band can be used to identify the existence of extracellular material in a given sample region as well as to estimate the amount of the extracellular material for purposes of scaling an observed spectral marker.

More importantly, the spectrum 22 of the connective tissue contains a spectral feature that is in the shape of a "shoulder" 30 at about 1280 cm⁻¹. The present invention is based on the discovery that the existence of this spectral feature is an effective indication of carcinoma. The existence of this spectral feature in a spectrum may be determined by examining the peak intensity about 1280 cm⁻¹ with respect to other portions of the spectrum. As used herein, "peak intensity" may be either peak height or peak area. An equivalent way of describing the existence of this "shoulder" is that the baseline of the band around 1280 cm$^{-1}$ has a positive slope (above a certain threshold). The slope of the baseline of the 1280 cm$^{-1}$ band serves as a marker for identifying the existence of the spectral feature. More particularly, a positive baseline slope of this band indicates that the area around the sample region is non-cancerous. Thus, for example, the positive baseline slope of the 1280 cm$^{-1}$ band in the spectrum 22 in FIG. 2 indicates that the region from which the spectrum was taken is non-cancerous.

In contrast, in samples from patients diagnosed by pathological studies as having breast cancer, the 1280 cm$^{-1}$ band is riding on a relatively flat baseline compared to that in samples of cancer-free patients, where the baseline associated with this band has a positive slope. The slope of the 1280 cm$^{-1}$ band is significant only in connective tissue regions of the sample, not in regions containing mainly epithelial cells.

Figure 3:
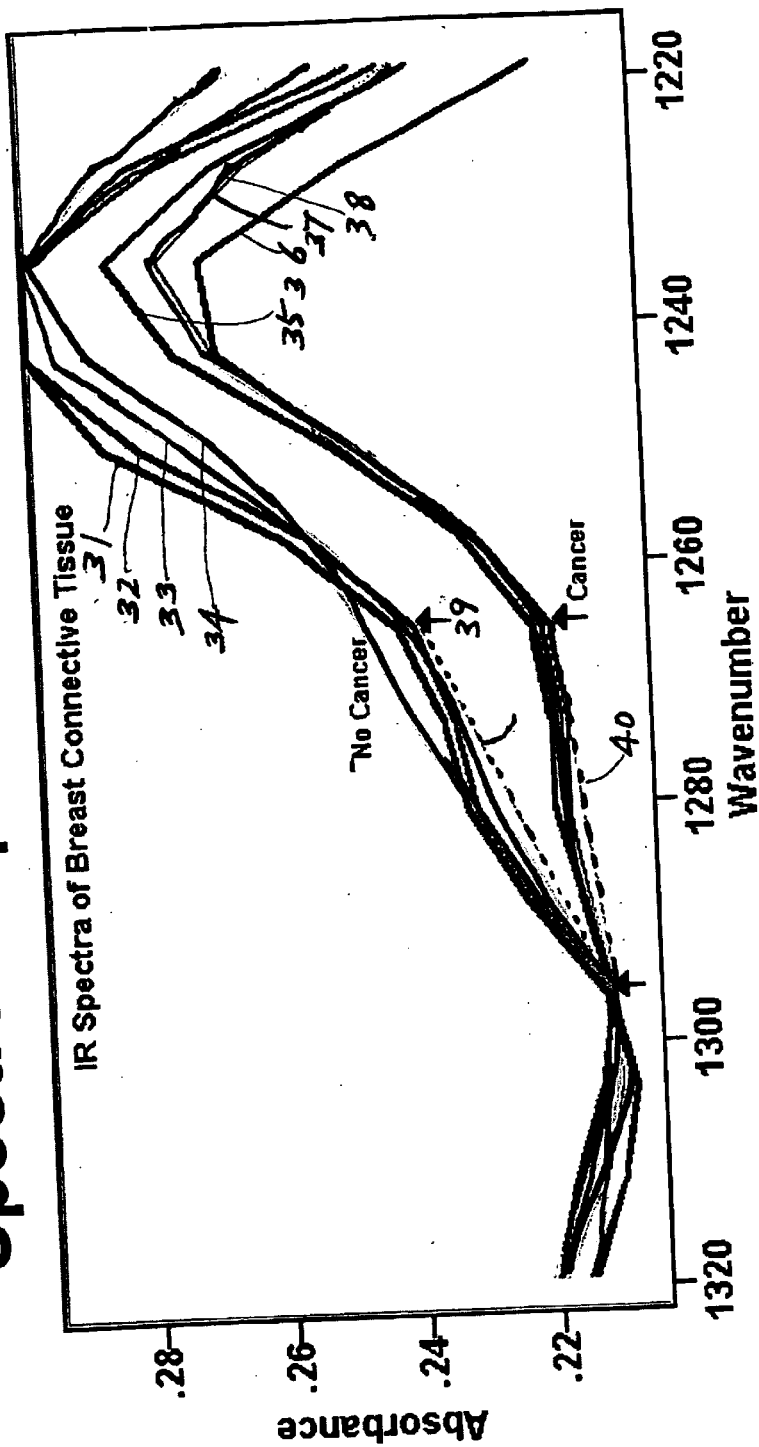
FIG. 3 shows mid-infrared spectra around a 1280 cm⁻¹ band taken from cancerous and non-cancerous breast biopsy samples, with the non-cancerous samples exhibiting a significantly more positive baseline slope for the 1280 cm⁻¹ band.

By way of example, FIG. 3 shows eight infrared spectra taken from different breast biopsy samples. The spectra 31–34 were taken from connective tissue regions in biopsy samples that were identified by pathologists as non-cancerous, while the spectra 35–38 were taken from connective tissue regions in biopsy samples identified by pathologists as cancerous. For illustration purposes, the baselines 39 and 40 between 1303 cm$^{-1}$ and 1264 cm$^{-1}$ are shown for the spectra 31 and 35, respectively.

As can be seen in FIG. 3, the baseline slopes of the 1280 cm$^{-1}$ band in the spectra 31–34 of the non-cancerous regions are all significantly more positive than those in the spectra 35–38 of the cancerous sample regions. The inventors of the present invention have discovered that the baseline slope in the IR spectrum between about 1303±8 cm$^{-1}$ and 1264±8 cm$^{-1}$ (identified by arrows in FIG. 3) in connective tissue regions is statistically strongly correlated with whether or not a patient has breast cancer. After examining 13 biopsy sample regions from six different patients, significant regions of higher slopes are only found in the connective tissue of cancer-free patients. In one performed study, the chosen baseline points for the 1280 cm$^{-1}$ band were at 1303 cm$^{-1}$ and 1264 cm$^{-1}$, and absorbance spectral intensities at these two points were measured using an infrared imaging device that has a focal-plane array (FPA) detector. Embodiments of the infrared imaging device are described in greater detail below. The slope of the baseline for the 1280 cm$^{-1}$ band were then obtained for each pixel in the image by simply subtracting the absorbance spectral image at 1303 cm$^{-1}$ from the corresponding image obtained at 1264 cm$^{-1}$. When the resulting difference image was plotted, the gray-scale level for each pixel is representative of the baseline slope in this sample.

Surprisingly, when this was done, connective tissue regions of high slope of the 1280 cm$^{-1}$ band stood out in the images of patient samples with no cancer, while no such effect was seen in patient samples identified as cancerous. A series of infrared images representing this slope was compared on exactly the same gray scale, and samples from patients without cancer were easily distinguished from samples from patients with cancer.

In a preferred embodiment, infrared spectral intensities at the two baseline points are measured by means of a focal plane array (FPA) detector with multiple pixels, which is capable of imaging a significant area of a biological sample at various infrared frequencies. Taking the infrared images of the sample allows sample regions containing extracellular material to be easily identified based on spectral features of the extracellular material as well as a comparison with the visual image of the sample.

As will be described in greater detail below, the imaging device may be set up such that a continuous spectrum is detected for each pixel of the detector. Alternatively, for purposes of practicing the invention, infrared spectral intensities only have to be measured at selected wavenumbers.

It will be appreciated, however, sample imaging with an FPA detector is preferred but not necessary for practicing the invention. For instance, an infrared image of the sample can be obtained with a single-element detector by point-by-point scanning. Moreover, no image has to be taken. Once a sample region containing extracellular material is identified, the infrared absorbance spectral intensities measured from that region can be used to determine the existence of the marker.

Thus, in accordance with the invention, the presence of pathology in a biological sample may be identified by finding an infrared spectral marker in the extracellular material in the biological sample. The term "pathology" as used herein includes abnormalities such as malignancy, infection, autoimmune conditions, endocrine abnormalities, abnormal immune responses, degenerative conditions and inflammatory processes, as well as early indications thereof.

Usually, the marker is located in connective tissue, but it could be anywhere in the extracellular material such as in lymph, blood (including blood constituents such as serum, plasma, the cellular components, protein fractions and the buffy coat), marrow, saliva, synovial fluid, cerebrospinal fluid, secretions or excretions such as urine and sweat.

Typically, extracellular material includes connective tissue matrix. This matrix can include any of the following: collagen, elastin, various glycoproteins, proteoglycans, and various extracellular matrix components. Collagen is an abundant protein in humans and animals. Presently, nineteen different varieties of collagen have been characterized in humans. A common feature of the collagens seems to be a triple-helical segment of variable length. Three polypeptide a-chains wrap around each other to form a rope-like structure. Elastin is composed of an insoluble protein polymer. It is often associated with microfibrils, which appear to be composed of certain glycoproteins such as fibrillin and microfibril-associated glycoproteins.

Other relevant glycoproteins that may be found in the extracellular matrix include the structural glycoproteins such as fibronectin, vitronectin, the thrombospondins, tenasin (also known as hexabrachion), and several leucine-rich repeat proteins such as decorin, biglycan, fibromodulin and lumican. Other more specialized glycoproteins are found in cartilage. Examples are cartilage oligomeric matrix protein (COMP, also known as thrombospondin-5) and leucine-rich repeat proteins such as PRELP and chondroadherin.

Proteoglycans are proteins having at least one polysaccharide chain. One of their functions appears to be to bind the matrix together. Specific examples are heparan sulfate proteoglycan, hyaluronan, syndecan, aggregan, versican, decorin, biglycan, fibromodulin, lumican and epiphycan.

While not wishing to be bound by theory, it is possible that the invention's extracellular marker for pathology is a consequence of any of the following: It may represent an area that has been cannibalized by the pathologic process, such as a cancer or an infection that takes nutrients from the extracellular area. These nutrients may be any of a number of extracellular constituents such as the proteins (e.g. collagen or elastin), glycoproteins or proteoglycans previously described. Alternatively, it is possible that the pathologic process results in metabolic waste, toxins or byproducts that are extruded into the extracellular region and produce a marker. The marker may be the extruded entity itself, or perhaps it results from a reaction between the extruded entity and extracellular constituents. Also, the marker may be due to the body producing a collagen-based barrier to surround the disease in order to keep it contained.

Theoretically, the wide scope of pathologies in which the invention finds application may be due to the distinctiveness of extracellular constituents such as connective tissue, particularly when studied spectroscopically. For example, it is known that the infrared absorption spectra of proteins vary with certain features such as the protein's secondary structure, hydration and ionic concentration of the solvent. Nevertheless, "the average infrared spectra of all metabolic and structural proteins found in cells turn out to be remarkably constant. The only proteins that exhibit distinctly different spectra are found in connective tissue (e.g., collagen)." Diem, et. al "Infrared Spectroscopy of Cells and tissues: Shining Light onto a Novel Subject," *Applied Spectroscopy* 53:4 (April 1999) 148A.

It is known that the cellular basement membrane is involved with the control of transport of fluids, ions, proteins and the like into or out of the cell. It is possible that a pathologic process, be it malignant, infectious, autoimmune or of other etiologies, may affect the basement membrane in such a way as to interfere with this membrane's transport mechanisms. It may follow that the basement membrane becomes more permeable or leaky in the face of a pathologic process. This in turn may be a theoretical basis for widespread applicability of the invention. That is, pathology affects the basement membrane's permeability with the result that substances leak out of the cell and perhaps accumulate in or damage the extracellular matrix and produce a marker. These substances may be normally occurring intracellular substances that find themselves in an abnormal location (extracellular) due to the leaky basement membrane. Alternatively, these substances may be toxic products, waste or other byproducts of the pathologic process or of the cell's attempt to react to the pathology.

Conventionally, basement membrane mechanics are believed to be especially relevant to diabetes mellitus, glomerulonephritis, the so-called collagen vascular diseases, the vasculitides and autoimmune diseases. Additionally, it is believed that malignancies affect the basement membrane before local extension or metastasis is evident by conventional testing. The group referred to as "collagen vascular disease" includes rheumatoid arthritis, systemic lupus erythromatosis, progressive systemic sclerosis, polymyositis, dermatospondylitis, Sjogren's Syndrome, arteritis, rheumatic fever, ankylosing spondylitis and amyloidosis.

The term "malignancy" includes carcinoma, sarcoma, lymphoma, blood dyscrasias, neuoroma, neuroblastoma, neoplasm, cancer and tumors. Carcinoma includes carcinomas of the breast, lung, colon, stomach, esophagus, small intestine, ovary, skin, pancreas and prostate. Melanomas are also included in the term. Sarcomas include abnormal growth of muscle, bone and cartilage such as osteomas, osteosarcomas, chondroblastomas and chondrosarcomas.

Lymphoma includes Hodgkin's and non-Hodgkin's varieties, such as small lymphocytic lymphoma, follicular lymphoma, small cleaved cell, large cell, mixed small and large cell, mantle cell, large B-cell with or without T cells, diffuse large B cell, large cell immunoblastic, precursor B lymphoblastic, small cell non-cleaved cell, Burkitt's and non-Burkitt's lymphoma, peripheral T-cell (unspecified) and precursor T cell lymphoblastic lymphomas.

Blood dyscrasias include leukemias such as acute and chronic varieties of the following: lymphocytic leukemia, monocytic leukemia, granulocytic leukemia and myeloblastic leukemia. Additional leukemias are undifferentiated leukemia, myeloid leukemia, promyelocytic, myelocytic, monocytic, erythro-leukemia, megakaryocytic, and lymphoid varieties of leukemia. Also included in the term "blood dyscrasias" are plasma cell disorders such as monoclonal gammopathies including malignant gammopathies such as multiple myeloma, plasma cell leukemia, non-secretory myeloma, plasmacytoma, Waldenstrom's macroglobulinemia, other lymphoproliferative disorders, heavy chain disease and primary amyloidosis.

Pathologies in addition to malignancies can be diagnosed or their risks assessed using the invention. The term "infection" includes bacterial, viral, richetsial, spirochete, mycoplasmal, protozoan and parasitic infections. Bacterial infections are infections caused by bacteria such as gram positive, gram negative or acid fast bacteria. Some examples of such bacteria are *streptococcus, staphylococcus, pneumococcus, enterococcus, E. coli, Klebsiela, pseudomonas, neisseria*, hydrogen bacteria, pyogenic bacteria, *bacteroides, proteus, hemophilus, treponema*, chlostridia, mycobacteria, nocardia and chlamydiae.

Viral infections include infections caused by the various hepatitis viruses causing the hepatides including hepatitis A, B, C, D, E, G and more recently F. Additional viruses causing infection as defined by the invention are human immunodeficiency virus (HIV), influenza virus, parainfluenza virus, respiratory syncytial virus, rhinovirus, coxsackie virus, retroviruses such as human T-lymphotrophic virus (types 1 and 2), leukemia virus, measles virus, papilloma virus, poliovirus, flavavirus, oncovirus, Epstein-Barr Virus, herpes simplex and herpes zoster.

Examples of richetsial infections include typhus, Q fever, ehrlichiosis and spotted fever such as Rocky Mountain spotted fever. Examples of spirochete infections are syphilis, relapsing fever, Lyme disease and leptospirosis. An example of mycoplasma infection is mycoplasma pneumonia, which accounts for 10% to 20% of all pneumonias. Examples of protozoal infectious agents are trichomonas and plasmodium, the latter of which causes malaria.

The term "inflammation" includes diseases or conditions having an inflammatory response. Essentially, the inflammatory response includes pain, swelling, redness or heat. Examples of inflammatory diseases or conditions include, but are not limited to, arthritis, hepatitis, immune complex disease, allergic reactions, inflammatory bowel disease, inflammatory carcinoma of the breast, inflammatory demyelinating conditions, inflammatory demyelinating polyneuropathy, Guillain-Barre syndrome, inflammatory polymyopathies, polyradiculoneuropathy, inflammatory diarrhea, dermatitis, thyroiditis and myositis.

The term "autoimmune" disease or condition refers to a condition characterized by a specific humoral or cellular mediated immune response against constituents of the body's own tissues, which may be referred to as self-antigens or autoantigens. Examples are lupus (including systemic lupus erythematosus), rheumatoid arthritis, aplastic anemia, diabetes mellitus, diabetes insipidus, Graves' disease, biliary cirrhosis, ataxic neuropathy, phemphigoid (both cicatricial and non-cicatricial varieties), hemolytic anemia, variants of hepatitis, hypoparathyroidism, idiopathic thrombocytopenia purpura, myasthenia gravis, multifocal motor neuropathy, paraneoplastic syndromes, scleroderma, Sjogren's syndrome and the diseases historically known collectively as the collagen vascular diseases.

Abnormal immune responses include the autoimmune diseases, allergic responses such as allergic rhinitis and anaphylaxis, and immune complex diseases that may cause serum sickness, hemolytic anemia, vasculitis, glomerulonephritis and cryoglobulinemia. Also included in the term are the primary immunodeficiency diseases such as X-linked agammaglobulinemia, common variable immunodeficiency, selective IgA deficiency, hyper-IgM, X-linked lymphoproliferative disease, DiGeorge syndrome, severe combined immunodeficiency disorders, combined immunodeficiency disorders, Wiskott-Aldrich Syndrome, defective expression of major histocompatibility complex antigens, ataxia-telangiectasia, hyper-IgE, leukocyte adhesion deficiencies and primary deficiencies of the complement system.

Endocrine abnormalities include diabetes mellitus (types I and II) and thyroid disorders such as Graves Disease, hypothyroidism, hyperthyroidism, thyroiditis and goiter. Additional examples are hypoparathyroidism, hyperparathyroidism, Cushing's Disease, adrenal corticohypertrophy, adrenal insufficiency, pancreatic islet cell disorder, multiple endocrine neoplasias (types 1 and 2), carcinoid syndrome, rickets and osteomalacia.

The term "degenerative change" means a degeneration in the normal function or structure of animal, including human, tissue. Examples include but are not limited to degenerative joint disease as well as degenerative neurological conditions such as Alzheimer's disease.

Figure 4:
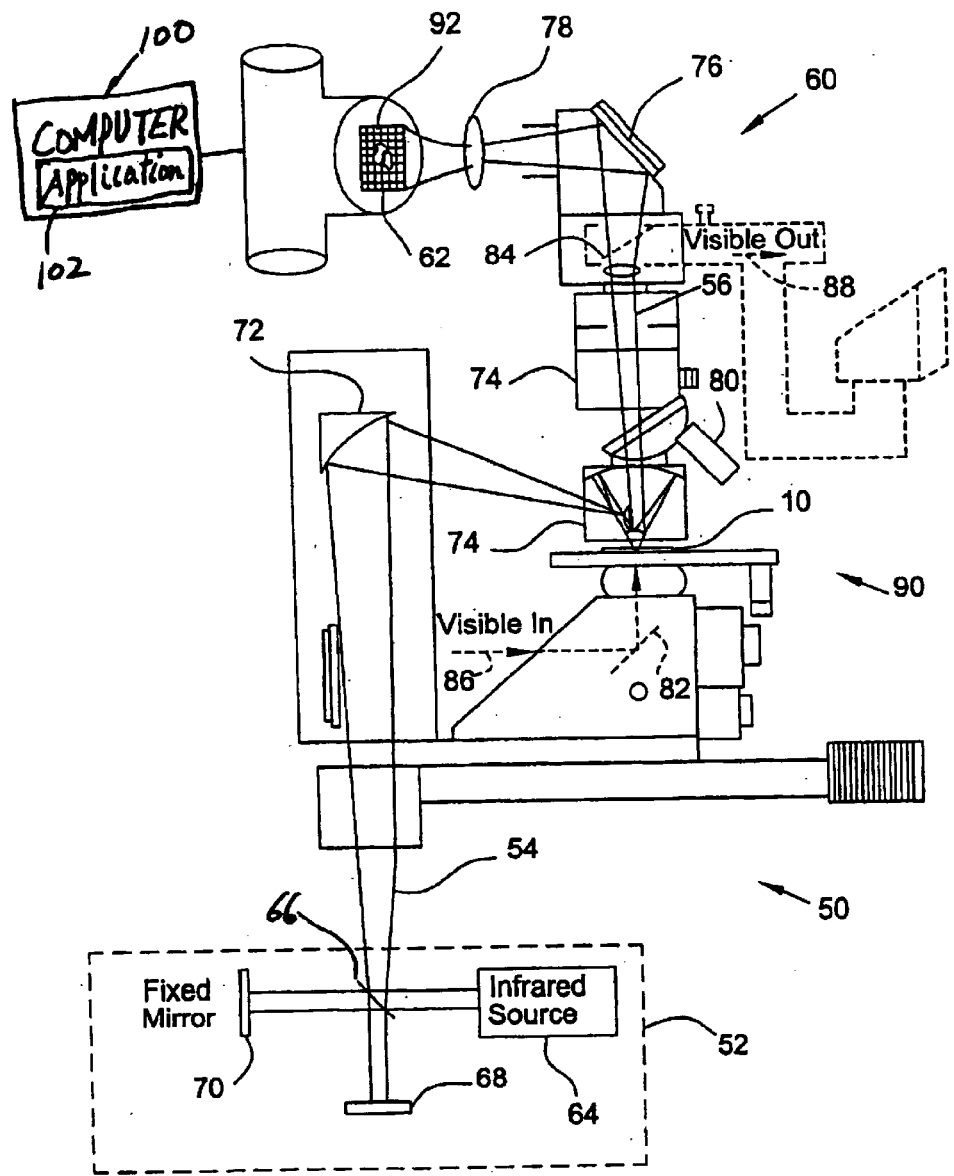
FIG. 4 is a schematic diagram showing a Fourier Transform Infrared (FT-IR) microspectroscopic imaging system for studying a biological sample according to the invention.

Referring now to FIG. 4, in one embodiment, biological samples are studied with the technique of the invention by means of a Fourier Transform Infrared (FT-IR) microspectroscopy imaging device that has a FPA detector 62 and a step-scanning FT-IR spectrometer 52 coupled to a refractive microscope. Such an infrared imaging device is described in U.S. Pat. No. 6,274,871, which is hereby incorporated by reference in its entirety.

The biological samples to be studied with this device are preferably each mounted on a slide that transmits visual light while reflecting infrared light in the mid-infrared region. Such a slide or window is described in U.S. Pat. No. 5,160,826 to Cohen, which is herein incorporated by reference in its entirety, and is commercially available from, for example, Kevley Technologies, Inc. in Chesterland, Ohio. The advantages of using such a slide with the infrared imaging device are described in U.S. Pat. No. 6,274,871 mentioned above. Specifically, the transparency of the substrate for visible light facilitates pathological studies of the biological sample based on visual examination. The reflectivity of the substrate for infrared light enables infrared analysis of the same sample using the infrared imaging spectroscopy technique.

In the illustrated embodiment of FIG. 4, the step-scan interferometer 52 includes a collimated glowbar infrared source 64. The infrared output of the source is partially reflected by a 50/50 beam splitter 66 to a movable step-scanning or rapid-scanning mirror 68 and partially transmitted to a fixed mirror 70. The reflected beam from the movable mirror and the reflected beam from the fixed mirror are partially combined by the beam splitter 66 to form the output beam 54 of the spectrometer 52. The spectrometer output beam 54 is reflected by a mirror 72 to a Cassegrainian mirror 74, which focuses the infrared light to the sample 10. The infrared light reflected by the substrate of the sample (and through the sample) is collected by the Cassegrainian mirror 74 and projected by a mirror 76 to a ZnSe lens 78, which focuses the infrared light from the sample onto the focal-plane array detector 62.

The microscope 60 includes an objective 80 for visual examination of the sample 10. To view the sample, the objective 80 is rotated into an operating position (which is the position occupied by the Cassegrainian mirror as shown in FIG. 4). Two mirrors 82 and 84 are also placed into their respective operation locations shown in FIG. 4. Visible input light 86 from the side is reflected by the mirror 82 through the substrate into the sample 10. Visible light transmitted through or scattered by the sample is collected by the objective 80 and reflected by the mirror 84 to the side. The output visible light 88 can be viewed by the user for identifying an area of interest (e.g., area with extracellular material) on the biological sample or collected to form a visible image (e.g., by means of a camera) that can be compared to the infrared images of the sample. The substrate carrying the sample is mounted on a stage 90, which can be moved to position an area of interest on the sample in place for FT-IR imaging.

During each FT-IR image acquisition process, the movable mirror 68 of the spectrometer 52 is step-scanned at pre-selected intervals. An infrared image of the sample 10 is taken at each scan step by measuring the infrared intensity detected by each pixel 92 in the array detector 62. The images of the sample taken at different scan steps, which are referred to as image interferograms, are processed by Fast Fourier Transformation (FFT) to generate a set of single-beam images, each corresponding to a wavenumber of infrared light.

To provide flat-field correction of the detected infrared signals, the same step-scan data acquisition is applied to a section of the substrate not covered by the biological sample to produce a set of background image interferograms and the corresponding background single-beam images. The single-beam images of the sample are numerically divided by the corresponding background single-beam images to produce a set of transmittance spectral images. The transmittance images are then processed (through a logarithmic function) to produce a set of absorbance spectral images corresponding to different wavenumbers of infrared light. Each absorbance spectral image is the spectral intensity of the sample at the wavenumber of that image. For each given pixel 92 of the detector, there is a corresponding pixel in each absorbance spectral image, and its spectral intensity values in the spectral images collectively form an absorbance spectrum of the sample portion imaged by that pixel.

As described above, the infrared spectra of the pixels can be used to identify regions of extracellular material and to identify the existence of an infrared spectral marker indicative of the presence of pathology in the sample. To perform the pathology diagnosis based on identification of infrared spectral markers, an area of interest on the biological sample is selected by visual inspection and positioned for FT-IR imaging in a reflection mode. Infrared light is directed to impinge on the sample for illumination. The infrared light reflected by the infrared-reflective substrate and through the sample is focused on the FPA detector with multiple pixels. The infrared images of the area of interest collected by the array detector are used to derive an infrared spectrum for each pixel of the array detector.

Regions of extracellular material, such as connective tissue, can be identified by infrared spectral features particular to the extracellular material. For instance, the infrared image of the sample at 1340 cm$^{-1}$ can be presented in gray scale to show the locations of the extracellular material. The locations of the extracellular material as revealed by the infrared image can also be confirmed by a comparison with the visual image of the sample. The infrared spectrum of a pixel corresponding to a region of extracellular material can then be analyzed to see whether it exhibits the marker indicative of pathology.

As mentioned above, in the case of breast cancer diagnosis, the marker is a flat (low slope) baseline of the 1280 cm$^{-1}$ band, and the slope can be derived from the difference in intensities at two baseline points, such as 1303 cm$^{-1}$ and 1264 cm$^{-1}$. In a preferred embodiment as shown in FIG. 4, the calculations of the baseline slope of the 1280 cm$^{-1}$ band is performed by a computer 100. The computer 100 is connected to the imaging system 60 for controlling the image acquisition operation and to receive intensity data of the pixels of the FPA detector in the imaging process. The computer has a software application 102 for FT-IR imaging data collection and spectroscopic image analysis. After obtaining the imaging data, the software is used to derive the slopes of the 1280 cm$^{-1}$ band baseline. This may be accomplished, for instance, by subtracting the infrared image at 1303 cm$^{-1}$ from the image at 1264 cm$^{-1}$.

Figure 5:
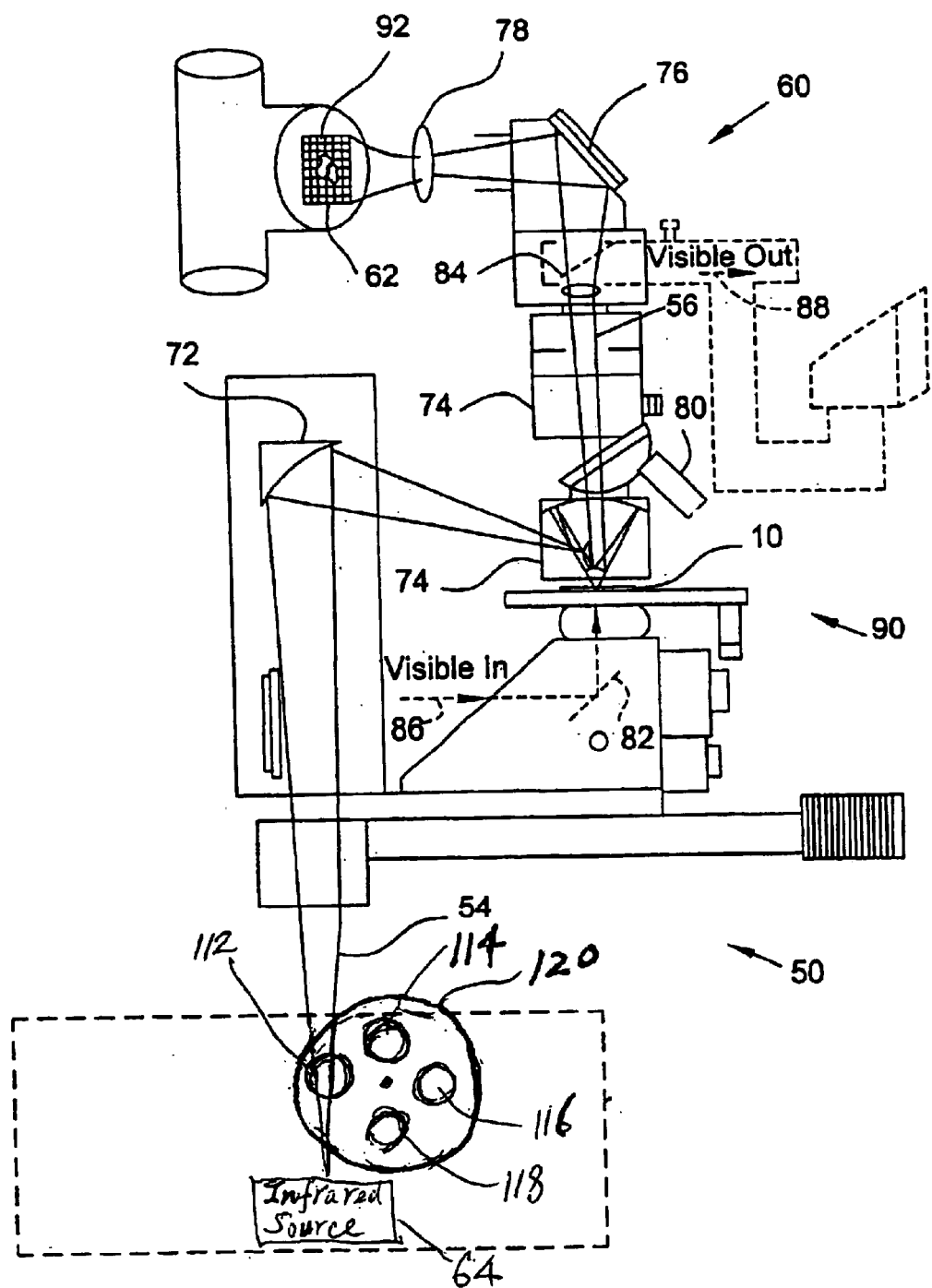
FIG. 5 is a schematic diagram showing a microspectroscopic imaging system similar to that of FIG. 4 but with narrow bandwidth input filters coupled to an infrared source for illuminating the sample with infrared light at selected wavenumbers.

As mentioned above, for the determination of the baseline slope, it is not necessary to measure an entire infrared spectrum for each imaging pixel. Rather, only infrared images at the two baseline points need to be taken. FIG. 5 shows an imaging device tailored for this application. This imaging device is basically the microspectroscopy imaging apparatus of FIG. 4, but with the FT-IR spectrometer 52 replaced by the combination of a wideband infrared source 64 coupled to narrow bandwidth infrared filters 112, 114, 116, and 118. As shown in FIG. 5, the filters are mounted on a filter wheel 120 such that each filter can be easily inserted in the path of the output light of the infrared source. The centers of the pass bands of two of the filters 112, 114 are around 1303 cm$^{-1}$ and 1264 cm$^{-1}$, respectively. Alternatively, the filter wheel 120 may be placed anywhere in the beam path between the infrared source and the array detector 62 without affecting the result of the experiment.

To take infrared images of the sample at 1303 cm$^{-1}$, the filter 112 is moved to the filtering position so that only infrared light in the narrow band around 1303 cm$^{-1}$ passes through the filter for illuminating the sample. The infrared image at 1264 cm$^{-1}$ is taken likewise with the filer 114 in place. The computer 10 then subtracts the infrared images taken with the two filters, and the resultant image is representative of the slope of the baseline of the 1280 cm$^{-1}$ band.

Alternatively, a circular (or linear) variable filter monochromator (or some other dispersive, acousto-optical tunable filter (AOTF), or liquid crystal tunable filter (LCTF) device) could be used to switch back and forth between the wavelengths of the two baseline points to obtain the slope measurement. Additionally, the marker can be measured using a single-element detector by subtraction of two spectral intensities at 1264 and 1303 cm$^{-1}$, as long as the region being sampled consists of mainly connective tissue.

In some types of samples, either due to the nature of the sample (such as the sample having a finite thickness or the sample being smeared, etc.) or the sample acquisition process, the extracellular material may not be completely separated from the cellular material. For such a sample, it may be advisable to scale the pathology marker described to the amount of extracellular material present in the region from which the infrared intensity data are taken. The fol-lowing example demonstrates the method of scaling the intensity data for deriving the breast cancer marker to the amount of connective tissue present in the sample region. This compensates for any existing differences in sample thickness, which could affect the absolute value of the baseline slope of the 1280 cm$^{-1}$ band.

The amount of connective tissue at any pixel location in the spectroscopic image can be determined by measuring the peak intensity (peak height or peak area) of the band centered at 1340 cm$^{-1}$. The baseline points for this band can be chosen as 1303±8 cm$^{-1}$ and 1366±8 cm$^{-1}$. To facilitate the measurement of infrared absorbance intensities at these two wavenumbers, the filter wheel is equipped with narrow bandwidth filters 116 and 118 that have their respective pass bands centered around these two wavenumbers. Infrared images at these two wavenumbers are taken by inserting the respective filter into the filtering position.

The baseline-corrected absorbance of the 1340 cm$^{-1}$ connective tissue band is defined as $A_{1340}-(A_{1303}+A_{1366})/2$ for each pixel in the image. Equivalently, the integrated area between the 1303 cm$^{-1}$ and 1366 cm$^{-1}$ data point on a spectral trace could be used to determine the intensity of the 1340 cm$^{-1}$ connective tissue band. To correct the slope of the baseline value between 1264 cm$^{-1}$ and 1303 cm$^{-1}$ described above for sample thickness, the intensity difference between 1264 cm$^{-1}$ and 1303 cm$^{-1}$ is divided by corrected intensity value of the peak at 1340 cm$^{-1}$. This calculation is shown below:

$$\frac{A_{1264} - A_{1303}}{A_{1340} - (A_{1303} + A_{1366})/2}$$

Note that this formula requires that there be an adequate amount of connective tissue. The denominator $A_{1340}-(A_{1303}+A_{1366})/2$ is preferably limited to a lower threshold to keep the result from becoming infinite when there is no net absorbance at 1340 cm$^{-1}$ above the baseline. The exact wavenumber positions of the filters used could be varied by about 8 cm$^{-1}$ greater or less than the stated wavelengths without significantly affecting the effectiveness of the marker identification.

Figure 6:
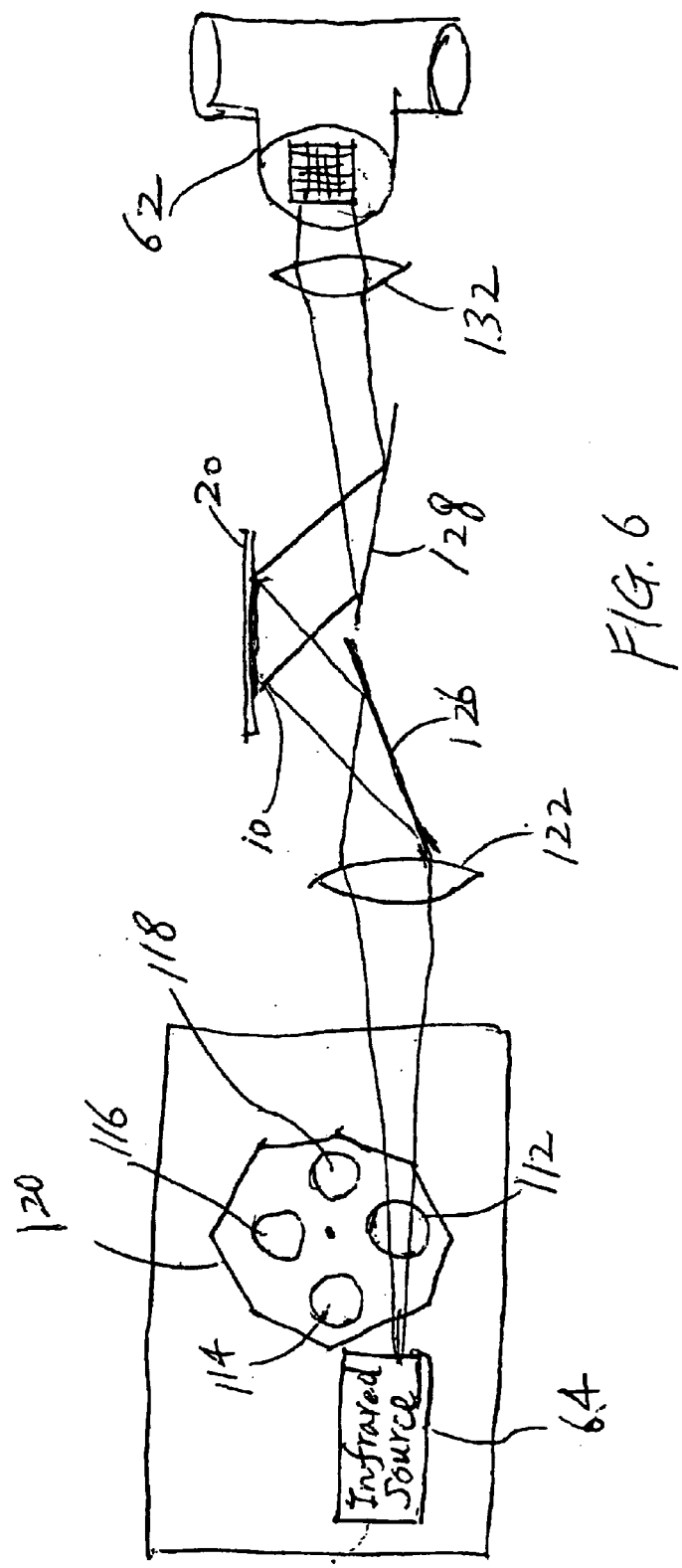
FIG. 6 is a schematic diagram showing a macroscopic infrared reflectance imaging device usable for collecting infrared images of a biological sample for spectral marker identification in accordance with the invention.

In another embodiment, a macroscopic reflectance spectroscopic imaging device is provided for allowing quick infrared image acquisition. Generally, for purpose of the invention, a spatial sample resolution (or granularity) of greater than about 1 millimeter is considered macroscopic. As shown in FIG. 6, the macroscopic imaging device utilizes the same infrared source/filter combination used in the embodiment of FIG. 5. In contrast to the embodiment of FIGS. 4 and 5, however, the infrared light through the filter is directed to the sample via a lens 122 (which may be replaced with a focusing mirror) and a plane mirror 126.

Alternatively, the combination of the wideband infrared source and filters may be replaced by the FT-IR spectrometer 52 shown in FIG. 4.

The sample 10 is mounted on the infrared-reflective slide 20 described above and is shown facing down in FIG. 6. Alternatively, the sample could be mounted on another IR-reflective substrate, or measured in transmittance on an IR-transparent substrate with or without an FPA. The infrared light reflected by the slide and through the sample is then collected and focused onto the FPA detector 62 by a plane mirror 128 and a lens 132 (which may be replaced with a focusing mirror).

A major advantage of this device is that a relative large sample area (e.g., ~1 cm×1 cm) can be imaged quickly at the selected wavenumbers. In one implementation, a bar target image showed a spatial resolution of 40 μm×40 μm per pixel when a 256×256 FPA detector was used. A total area of 1 cm×1 cm on the sample was imaged, although there was signal lost at the corners of the image, due to vignetting. Using this setup, it was possible to image an entire stain breast biopsy section that was mounted on an infrared-reflective glass microscope slide.

Thus, by first examining a specimen using this imaging device, one can get an overview of the entire sample to see if there are any specific spectroscopic indications of abnormalities (e.g., disease, cancer, etc.) before rerunning the sample under higher magnification in the FT-IR microscope, where the spatial resolution is increased to 3 μm×3 μm per pixel (with a 256×256 FPA) or 10 μm×10 μm per pixel (with a 64×64 FPA) in place on the microscope.

It can be appreciated from the foregoing detailed description that the invention provides a method and system for diagnosing pathology in a biological sample based on infrared spectral markers in an extracellular material. This new approach provides an alternative to or compliments the conventional pathological study for reliable identification of pathology.

What is claimed is:

1. A method of diagnosing the presence of pathology in a biological sample, comprising the steps of:
   identifying a region in the biological sample containing an extracellular material;
   obtaining infrared absorbance spectral data from the region containing the extracellular material; and
   determining, from the infrared absorbance spectral data, whether an infrared spectral marker is found in the region containing the extracellular material, wherein finding the infrared spectral marker is indicative of presence of pathology in the biological sample, and wherein the infrared spectral marker is a relatively flat baseline of an infrared band at about 1280 cm$^{-1}$.

2. A method as in claim 1, wherein the extracellular material is connective tissue.

3. A method as in claim 1, wherein the pathology to be diagnosed is carcinoma.

4. A method as in claim 1, wherein the biological sample is a breast biopsy sample, and wherein the pathology to be diagnosed is breast cancer.

5. A method of diagnosing the presence of pathology in a biological sample, comprising the steps of:
   identifying a region in the biological sample containing an extracellular material;
   obtaining infrared absorbance spectral data from the region containing the extracellular material; and
   determining, from the infrared absorbance spectral data, whether an infrared spectral marker is found in the region containing the extracellular material, wherein finding the infrared spectral marker is indicative of presence of pathology in the biological sample, wherein the infrared spectral marker is a relatively flat baseline of an infrared band at about 1280 cm$^{-1}$, and wherein the determining includes calculating a slope of the baseline of the infrared absorbance spectral band at about 1280 cm$^{-1}$ from infrared absorbance spectral intensities of a first baseline point wavenumber adjacent and greater than 1280 cm$^{-1}$ and a second baseline point wavenumber adjacent and smaller than 1280 cm$^{-1}$.

6. A method as in claim 5, wherein the step of obtaining infrared absorbance spectral data includes measuring the infrared absorbance spectral intensities at the first and second baseline point wavenumbers from the region containing the extracellular material.

7. A method as in claim 6, wherein the step of measuring the infrared absorbance spectral intensities includes detecting an infrared image of the biological sample at the first baseline point wavenumber and detecting an infrared image of the biological sample at the second baseline point wavenumber.

8. A method as in claim 7, wherein the steps of detecting the infrared images use a focal plane array detector having multiple pixels to detect infrared light from the biological sample.

9. A method as in claim 7, wherein the step of determining whether the infrared spectral marker is found includes subtracting the infrared image at the second baseline point wavenumber from the infrared image at the first baseline point wavenumber to generate a difference image.

10. A method as in claim 9, further including the step of presenting the difference image for viewing.

11. A method as in claim 7, wherein the steps of detecting the infrared images include illuminating the biological sample with narrow bands of infrared light at the first and second baseline point wavenumbers, respectively, through the use of narrow bandwidth infrared filters.

12. A method as in claim 5, wherein the step of calculating the slope of the baseline of the infrared absorbance spectral band at about 1280 cm$^{-1}$ includes deriving an intensity difference between infrared absorbance spectral intensities at the first and second baseline point wavenumbers and scaling the intensity difference with a correct peak intensity of an infrared absorbance peak associated with the extracellular material.

13. A method as in claim 12, wherein the infrared absorbance peak associated with the extracellular material is at a wavenumber of about 1340 cm$^{-1}$.

14. A method as in claim 13, including the step of calculating the corrected peak intensity from a measured peak intensity of the infrared absorbance peak and measured baseline intensities of the infrared absorbance peak.

15. A method as in claim 5, wherein the first and second baseline point wavenumbers are about 1303 cm$^{-1}$ and 1264 cm$^{-1}$, respectively.

* * * * *